US011938200B2

(12) United States Patent
Reddy et al.

(10) Patent No.: US 11,938,200 B2
(45) Date of Patent: Mar. 26, 2024

(54) NON-NUTRITIVE SWEETENERS AND POLYOLS AS IMAGING AGENTS

(71) Applicants: THE TRUSTEES OF THE UNIVERSITY OF PENNSYLVANIA, Philadelphia, PA (US); SIDRA MEDICINE, Doha (QA)

(72) Inventors: Ravinder Reddy, Gladwyne, PA (US); Mohammad Haris, Doha (QA); Hari Hariharan, Mount Laurel, NJ (US); Puneet Bagga, Philadelphia, PA (US); Francesco M. Marincola, Palo Alto, CA (US); Mitchell D. Schnall, Wayne, PA (US)

(73) Assignees: The Trustees of the University of Pennsylvania, Philadelphia, PA (US); Sidra Medicine, Doha (QA)

( * ) Notice: Subject to any disclaimer, the term of this patent is extended or adjusted under 35 U.S.C. 154(b) by 2 days.

(21) Appl. No.: 16/075,395

(22) PCT Filed: Feb. 3, 2017

(86) PCT No.: PCT/US2017/016473
§ 371 (c)(1),
(2) Date: Aug. 3, 2018

(87) PCT Pub. No.: WO2017/136700
PCT Pub. Date: Aug. 10, 2017

(65) Prior Publication Data
US 2018/0369427 A1 Dec. 27, 2018

Related U.S. Application Data

(60) Provisional application No. 62/291,949, filed on Feb. 5, 2016.

(51) Int. Cl.
*A61K 49/06* (2006.01)
*A61B 5/055* (2006.01)
*A61K 49/10* (2006.01)
*A61K 51/04* (2006.01)
*G01R 33/56* (2006.01)
*A61B 6/03* (2006.01)

(52) U.S. Cl.
CPC .............. *A61K 49/06* (2013.01); *A61B 5/055* (2013.01); *A61K 49/108* (2013.01); *A61K 51/0421* (2013.01); *A61K 51/0491* (2013.01); *G01R 33/5601* (2013.01); *A61B 6/037* (2013.01)

(58) Field of Classification Search
CPC ...... A61K 51/04; A61K 49/06; A61K 49/108; A61B 5/055
See application file for complete search history.

(56) References Cited

U.S. PATENT DOCUMENTS

| 5,121,059 A | 6/1992 | Wieland |
| 6,963,769 B1* | 11/2005 | Balaban ................ A61B 5/055 |
| | | 324/307 |
| 8,278,925 B2* | 10/2012 | Sun .................... G01R 33/4828 |
| | | 324/307 |
| 8,686,727 B2 | 4/2014 | Reddy et al. |
| 9,157,976 B2 | 10/2015 | Reddy et al. |
| 2005/0059881 A1 | 3/2005 | Balaban et al. |
| 2006/0051480 A1 | 3/2006 | Miles |
| 2011/0176999 A1* | 7/2011 | Quagliano ........... A61K 9/0095 |
| | | 424/9.1 |
| 2014/0142180 A1 | 5/2014 | Birsoy et al. |
| 2014/0154185 A1 | 6/2014 | Van et al. |
| 2014/0213887 A1 | 7/2014 | Reddy et al. |
| 2014/0288411 A1 | 9/2014 | Shapiro et al. |
| 2015/0086484 A1 | 3/2015 | Hanes et al. |
| 2016/0081575 A1 | 3/2016 | Wu |
| 2016/0081578 A1 | 3/2016 | Gazit et al. |

FOREIGN PATENT DOCUMENTS

WO 2008/020765 A2 2/2008

OTHER PUBLICATIONS

Cheng, V.Y., et al., "Impact of carbohydrate restriction with and without fatty acid loading on myocardial 18F-FDG uptake during PET:A randomized controlled trial" J. Nucl. Cardiol, pp. 286-291 (Year: 2010).*
Arrieta, M.C., et al., "Alterations in Intestinal Permeability", Gut, pp. 1512-1520 (Year: 2005).*
Bornemann, V., et al., "Intestinal Metabolism and Bioaccumulation of Sucralose in Adipose Tissue in the Rat", J. Tox. Env. Health, Part A., pp. 913-923 (Year: 2018).*
Walter H. Kaye et al. Sucrose activates human taste pathways differently from artificial sweetener, NeuroImage, 39, 1559-1569. (Year: 2008).*
Weinstein, et al., Imaging Enterobacteriaceae infection in vivo with 18F-fluorodeoxysorbitol positron emission tomography. Science Translational Medicine, Oct. 22, 2014, 6(259):259ra146.
Walker-Samuel, et al., In vivo imaging of glucose uptake and metabolism in tumors. Nature Medicine, Aug. 2013, 19(8):1067-72.
Testa, et al., Prodrugs Revisited: The "Ad Hoc" Approach as a Complement to Ligand Design. Medicinal Research Reviews, 16(3):233-241.

(Continued)

*Primary Examiner* — Michael G. Hartley
*Assistant Examiner* — Jagadishwar R Samala
(74) *Attorney, Agent, or Firm* — BakerHostetler (57) ABSTRACT

The present disclosure relates to magnetic resonance imaging (MRI) methods comprising (i) obtaining a baseline chemical exchange saturation transfer (CEST) MRI image of a patient, (ii) administering an effective amount of a non-nutritive sweetener to the patient, and (iii) obtaining one or more test CEST MRI image of the patient subsequent to the administering step (ii); wherein the step (i) and (iii) acquisition parameters are substantially the same. The non-nutritive sweetener may include a natural or artificial sugar alcohol, polyol, or combinations or derivatives thereof.

12 Claims, 4 Drawing Sheets

(56) References Cited

OTHER PUBLICATIONS

Nasrallah, et al., Imaging brain deoxyglucose uptake and metabolism by glucoCEST MRI. Journal of Cerebral Blood Flow and Metabolism, May 15, 2013, 33(8):1270-8.
Kogan, et al. Method for high-resolution imaging of creatine in vivo using chemical exchange saturation transfer. Magn. Reson. Med., 2013, 71:164-72.
Kogan, et al., Chemical Exchange Saturation Transfer (CEST) Imaging: Description of Technique and Potential Clinical Applications. Current Radiology Reports, Jun. 1, 2013, 1(2): 102-114.
Greenwood, et al., Hyperosmolar opening of the blood brain barrier in the energy depleted rat brain. Part 1. Permeability studies. J. Cerebral Blood Flow and Metabolism, 1988, 8(1):9-15.
Cai, Magnetic Resonance Imaging of Glutamate. Nature Medicine, 2012, 18(2), 302-306.
Barney, et al., A Pilot Study Comparing FLT-PET and FDG-PET in the Evaluation of Response to Cetuximab and Radiation Therapy in Advanced Head and Neck Malignancies. Journal of Nuclear Medicine and Radiation Therapy. Feb. 5, 2012, 3:1-6.
Alauddin, Positron emission tomography (PET) imaging with 18F-based radiotracers. American Journal of Nuclear Medicine and Molecular Imaging, 2012, 2(1):55-76.
DeBrosse et al., "Lactate Chemical Exchange Saturation Transfer (LATEST) Imaging in vivo a Biomarker for LDH Activity", Scientific Reports, Jan. 22, 2016, 1-9.

* cited by examiner

NON-NUTRITIVE SWEETENERS AND POLYOLS AS IMAGING AGENTS

CROSS-REFERENCE TO RELATED APPLICATIONS

This application is the National Stage Application of International Patent Application No. PCT/US2017/016473, filed Feb. 3, 2017, which claims priority to U.S. Provisional Patent Application No. 62/291,949, filed Feb. 5, 2016, both of which applications are herein incorporated by reference in their entireties for any and all purposes.

GOVERNMENT RIGHTS

This invention was made with government support under grant numbers EB015893 and NS087516 awarded by the National Institutes of Health. The government has certain rights in the invention.

TECHNICAL FIELD

This invention relates generally to the use of non-nutritive sweeteners as imaging agents.

BACKGROUND

Positron Emission Tomography (PET) has gained widespread attention as a molecular and metabolic imaging modality of cancers and other human diseases. Different PET tracers have been developed to detect the pathologies in vivo based on their differential uptake rate or binding to specific molecules or receptors. PET based imaging of fluoro-deoxyglucose $^{18}$F (FDG) is widely used to detect and study tumors and inflammatory process in different pathologies based on its uptake rate and glycolytic activity of tumors. Although widely used, one challenge of this approach is that it requires radiolabeled agents that preclude frequent repeated scans to assess the disease progression or drug response. Because FDG-PET is not cancer specific to tumor cells only, it will accumulate in areas especially with high levels of metabolic activity. Consequently, increased uptake is possible in tissue regions of hyperactivity, inflammation, tissue repair, and the like. Because cancer cells are hyper metabolic and consume more FDG than the healthy cells, this difference in the FDG uptake provides the contrast in the tumor in PET image. However, because PET produces high degree of background signal from healthy tissues, it is difficult to detect subtle changes in the early stages of the tumor; Thus it may produce false negatives from low grade tumors with glycolytic activity comparable to healthy tissue Gadolinium based contrast agents, such as gadolinium-diethylenetriaminepentaacetic acid (Gd-DTPA), also are widely used in clinical diagnosis of tumors and other pathologies using magnetic resonance imaging (MRI). However, these contrast agents are contraindicated for patients with renal insufficiency and diabetes.

Glucose CEST (GlucoCEST) is another MRI method that uses D-glucose infusion to study tumors. However, because D-glucose is readily metabolized by tumors and healthy tissue, GlucoCEST does not highlight the tumor but instead shows the residual extracellular glucose and it may not highlight the actual tumor. Further, GlucoCEST requires infusion of high concentration of D-glucose and, accordingly, may not be useful in studying diabetic patients.

Accordingly, reliable imaging agents are needed which can be safely administered to patients afflicted with various conditions.

SUMMARY

In some embodiments, imaging methods are provided and comprise (i) administering an effective amount of a non-nutritive sweetener to a patient; and (ii) obtaining one or more images of said patient subsequent to administering step (i). In certain aspects, the imaging is magnetic resonance imaging (MRI). In other aspects, the imaging is positron emission topography (PET).

In further embodiments, MRI methods are provided and include (i) obtaining a baseline chemical exchange saturation transfer (CEST) MRI image of a patient; (ii) administering an effective amount of a non-nutritive sweetener to said patient; and (iii) obtaining one or more test CEST MRI image of said patient subsequent to the administering step (ii). The acquisition parameters in steps (i) and (iii) may be substantially the same or differ.

In other embodiments, methods of monitoring the effectiveness of a pharmaceutical agent in treating a condition in a patient are provided and include (i) obtaining a baseline conventional MRI image and a baseline CEST MRI image of said patient; (ii) administering a pharmaceutical agent to said patient; (iii) administering an effective amount of a non-nutritive sweetener to said patient; and (iv) obtaining one or more test CEST MRI image of said patient.

In yet further embodiments, methods of distinguishing abnormal tissue from normal tissue in a patient are provided and include (i) obtaining a baseline CEST MRI image of said patient; (ii) administering an effective amount of a non-nutritive sweetener to said patient; and (iii) obtaining one or more test CEST MRI image of said patient.

In still other embodiments, methods of analyzing a magnetic resonance imaging (MRI) contrast agent are provided and include (i) obtaining a baseline CEST MRI image of said patient; (ii) administering a MRI contrast agent to said patient; (iii) administering an effective amount of a non-nutritive sweetener to said patient; and (iv) obtaining one or more test CEST MRI image of said patient.

In yet further embodiments, methods of analyzing the effect of a nutritive sugar on tumor cells in a patient are provided and include (i) obtaining a baseline CEST MRI image of said patient; (ii) administering a nutritive sugar to said patient; (iii) administering an effective amount of a non-nutritive sweetener to said patient; and (iv) obtaining one or more test CEST MRI image of said patient.

In other embodiments, PET imaging methods are provided and comprise (i) administering to a patient an effective amount of a non-nutritive sweetener comprising one or more radiolabels; and (ii) obtaining one or more test PET images of said patient subsequent to administering step (i).

In further embodiments, methods of monitoring the effectiveness of a pharmaceutical agent in treating a condition in a patient are provided and comprise (i) administering a pharmaceutical agent to said patient; (ii) administering an effective amount of a non-nutritive sweetener comprising one or more radiolabels to said patient; and (iii) obtaining one or more positron emission tomography (PET) images of said patient.

In still other embodiments, methods of distinguishing abnormal tissue from normal tissue in a patient are provided and comprise (i) administering an effective amount of a non-nutritive sweetener comprising one or more radiolabel to said patient; and (ii) obtaining one or more PET images of said patient.

In yet further embodiments, methods of analyzing a PET radiotracer in a patient are provided and comprise (i) administering a PET radiotracer to said patient; (ii) administering an effective amount of a non-nutritive sweetener comprising one or more radiolabel to said patient; and (iii) obtaining one or more PET images of said patient.

In other embodiments, methods of analyzing the effect of a nutritive sugar on tumor cells in a patient are provided and comprise (i) administering a nutritive sugar to said patient; (iii) administering an effective amount of a non-nutritive sweetener comprising one or more radiolabel to said patient; and (iv) obtaining one or more PET images of said patient.

In still further embodiments, methods of analyzing the blood brain barrier of a patient are provided and comprise (i) administering an effective amount of a non-nutritive sweetener comprising one or more radiolabel to said patient; and (ii) measuring the amount of said non-nutritive sweeter which accumulates in the brain of said patient after administering step (i).

Other aspects and embodiments of the invention will be readily apparent from the following detailed description of the invention.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific compositions, methods, devices, and systems disclosed. In addition, the drawings are not necessarily drawn to scale.

DETAILED DESCRIPTION OF ILLUSTRATIVE EMBODIMENTS

The inventors found that imaging methods, such as MRI and PET, may be performed using non-nutritive sweeteners. Because non-nutritive sugars such as sucralose don't cross the blood brain barrier (BBB), their use in the imaging methods described herein permit the identified of cancer tissues, among others. Furthermore, because non-nutritive sweeteners such as sucralose show no toxicity at very high doses, they can be used as both MRI contrast and PET imaging agent. Thus, both MRI and PET imaging can be performed in the same setting, which has the advantage of improving monitoring of tumor relapse and treatment and in vivo or ex vivo as preferred by those skilled in the art.

As such the imaging methods described herein comprise administering an effective amount of a non-nutritive sweetener to a patient and obtaining one or more images of said patient subsequent to administering step (i). Additional steps, image gathering, or reagents as necessitated by the particular method may be included as understood in the art and/or as described below for specific techniques.

When utilized as MRI contrast agents, the methods may be repeated as needed because they do not utilize radioactive ligands. Nor do the methods described herein require costly hyper polarization methods and may be performed in the absence of a radiolabeled imaging agent, contrast agent, and glucose, among others.

When utilized as PET imaging agents, the methods successfully highlight tumors and simultaneously provide negligible background contrast. The non-nutritive sweeteners, particularly sucralose, have significant noteworthy features over FDG when utilized in the PET imaging methods described herein. Of significance, because many of the non-nutritive sugars are not taken up by cells, they accumulate in the tumors due to enhanced permeability and retention effect, thereby reducing false positive and false negative results.

In the present disclosure the singular forms "a", "an" and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" or "substantially" it will be understood that the particular value forms another embodiment. In general, use of the term "about" or "substantially" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about" or "substantially". In other cases, the gradations used in a series of values may be used to determine the intended range available to the term "about" or "substantially" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

The terms "patient" or "subject" as used herein are interchangeable and refer to a mammalian animal. In one embodiment, the patient or subject is a human. In another embodiment, the patient or subject is a veterinary or farm animal, a domestic animal or pet, or animal normally used for clinical research. In some preferred embodiments, the patient has elevated blood glucose levels where additional precautions may be required prior to a PET scan using FDG. In other preferred embodiments, the patient has high blood glucose levels. In further preferred embodiments, the patient has a blood glucose level of about 150 mg/DL or greater.

The term "image" as used herein refers to a single image or two or more images, i.e., a set of images or "image set." The image may be obtained from a single location in the patient or two or more locations in the patient, i.e., multi-slice images.

A. MRI Methods

The MRI methods described herein utilized chemical exchange saturation transfer (CEST) MRI techniques known in the art. See, e.g., Cai, Nature Medicine, 18, 302, 2012; Kogan, Current Radiology Reports, 1(2): 102-114, Jun. 1, 2013; and US Patent Publication No. 2012/0019245, which are incorporated by reference. In CEST MRI, regional variations in the following parameters viz., exchange rates, $T_2^*$, $T_1$, $T_2$ and $T_1\rho$ are imaged using measurements recognized in the art. In some embodiments, one or more of these parameters is measured directly. In other embodiments, dynamic changes in these parameters are measured either through direct measurement of parameter maps or through measurement of images that exhibit contrast based on the changes in these parameters. In further embodiments, CEST MRI may be performed before and/or after infusion of non-nutritive sweeteners.

As in conventional MRI techniques, a baseline CEST MRI image of a patient may be obtained. The term "baseline" as used herein refers to a CEST MRI image obtained of the patient prior to the administration of any exogenous agents. The baseline CEST MRI image is obtained using a defined set of acquisition parameters, which may be selected by those skilled in the art. In some embodiments, the acquisition parameters depend on the non-nutritive sweetener selected for use herein as described below.

After the baseline image is obtained, an imaging agent is administered to the patient. Unlike the GlucoCEST imaging methods, the methods described herein are performed using imaging agents which are not metabolized by tumors. The imaging agents useful herein are classified generally as non-nutritive sweeteners.

After administration of the non-nutritive sweetener, one or more test CEST MRI images of the patient are obtained. The number of test images acquired includes a sufficient number of MRI images to fully define and analyze the portion of the patient being analyzed. One of skill in the art would readily be able to determine the number of test images required to obtain a reliable and clear image of the patient. In some embodiments, one or more CEST MRI images are obtained. In other embodiments, two or more, i.e., multiple, CEST MRI images are obtained. By doing so, wash-in/wash-out kinetics with multiple images or a single image may be measured.

The test images are obtained using acquisition parameters which depend on a number of factors including, without limitation, the results of the baseline image, non-nutritive sweetener selected for use herein, subject, among others. In some embodiments, the acquisition parameters utilized to acquire the one or more test images are substantially the same as the acquisition parameters utilized to obtain the baseline image. In other embodiments, the acquisition parameters utilized to acquire the one or more test images differ from the acquisition parameters utilized to obtain the baseline image.

After the baseline and test CEST MRI images have been obtained, they are compared using skill in the art to obtain a final image. In some embodiments, a plurality of test CEST MRI images is obtained and compared with the baseline CEST MRI image over a period of time. In some embodiments, the CEST MRI scans are used to compute wash-in and wash-out kinetics for the nonnutritive sweetener induced contrast.

B. PET Methods

The PET imaging described herein is performed using techniques known to those skilled the art. See, e.g., Alauddin, American Journal of Nuclear Medicine and Molecular Imaging, 2012, 2(1):55-76, which is incorporated herein by reference. However, instead of trimethoprim, a radiolabeled non-nutritive sweetener is utilized. The PET imaging method described herein comprises administering to a patient an effective amount of a non-nutritive sweetener comprising one or more radiolabels. After administration of the non-nutritive sweetener, one or more test PET images of the patient are obtained.

As in conventional and CEST MRI techniques, a baseline PET image of a patient may be obtained. The term "baseline PET image" as used herein refers to a PET image obtained of the patient prior to the administration of any exogenous agents. The baseline PET image is obtained at some point prior to acquiring the PET images. The baseline PET images are obtained using a defined set of acquisition parameters, which may be selected by those skilled in the art. In some embodiments, the acquisition parameters depend on the non-nutritive sweetener selected for use herein as described below. In some embodiments, a plurality of test PET images is obtained.

After the one or more PET images are obtained, the test PET images are reconstructed in a medium sensible to an operator. The final PET images may be optionally compared with the baseline PET image using skill in the art to obtain a final image.

C. The Non-Nutritive Sweetener

The term "non-nutritive sweetener" as used herein refers to a chemical compound which is not metabolized by healthy tissue. When utilized for MRI, the non-nutritive sweetener contains at least one proton which can be utilized in chemical exchange saturation transfer imaging methods. In some embodiments, the non-nutritive sweetener exhibits CEST with bulk water in a concentration and pH dependent manner. In other embodiments, the CEST MRI image obtained after administration of the non-nutritive sweetener exhibits a contrast that is dependent on both the local concentration of the sweetener and local pH in the tissue of interest. By doing so, the methods described herein permit rapid data collection facilitating the measurement of the wash-in and wash-out kinetics of the non-nutritive sweeteners in different pathologies.

When utilized for PET imaging, the non-nutritive sweetener is radiolabeled. The term "radiolabeled" as used herein refers one or more chemical moieties which contain a radioactive isotope which is bound to the non-nutritive sweetener. In some embodiments, the non-nutritive sweetener contains at least one radiolabel. In other embodiments, the non-nutritive sweetener contains at least two radiolabels. In further embodiments, the non-nutritive sweetener contains at least three radiolabels. In still other embodiments, the non-nutritive sweetener contains at least four, five, six, seven, eight, or nine radiotracers. In yet further embodiments, the radioactive isotope is a radiolabeled halogen or radiolabeled carbon atom. In other embodiments, the radiolabel is $O^{11}$, $^{11}C$, $^{18}F$, $^{123}I$, $^{125}I$, $^{124}I$, $^{131}I$, $^{32}Cl$, $^{33}Cl$, $^{34}Cl$, $^{74}Br$, $^{75}Br$, $^{76}Br$, $^{77}Br$, $^{78}Br$, or combinations thereof. In further embodiments, the radiolabel is $^{11}C$, $^{18}F$, $^{36}Cl$, $^{76}Br$, $^{123}I$, $^{124}I$, $^{125}I$, or $^{131}I$, or combinations thereof. In preferred embodiments, the radiolabel is $^{11}C$. In further preferred embodiments, the non-nutritive sweetener contains one $^{11}C$ radiolabel. In yet other preferred embodiments, the radiolabel is $^{36}Cl$. In still other preferred embodiments, the non-nutritive sweetener contains three $^{36}Cl$ atoms. In further preferred embodiments, the non-nutritive sweetener is:

The non-nutritive sweetener may be naturally occurring or synthetically derived. In some embodiments, the non-nutritive sweetener contains at least one hydroxyl group, amide group, amine group proton, or combinations thereof. In other embodiments, the non-nutritive sweetener is aspartame (Equal®, Nutrasweet®), neotame, acesuflame potassium (Sweet One®, Sunett®), sucralose (Splenda®), cyclamate, saccharin (SugarTwin®, Sweet'nLow®), stevioside, rebaudioside (Pure Via®), steviol, or combinations or derivatives thereof. In some preferred embodiments, the non-nutritive sweetener is sucralose. In further embodiments, the non-nutritive sweetener is a sugar alcohol or polyol. In still other embodiments, the non-nutritive sweetener is a sugar alcohol. In yet further embodiments, the non-nutritive sweetener is sorbitol, xylitol, erythritol, mannitol, maltitol, lactitol, erythritol, or combinations or derivatives thereof. Advantageously, many sweeteners already approved by the Food and Drug Administration for consumption may be utilized in the methods described herein.

Tautomeric forms of the non-nutritive sweeteners may also utilized. In some embodiments, the tautomeric form of the non-nutritive sweetener has the necessary bioactivity for use herein. Further, the non-nutritive sweeteners may also be used in the form of salts derived from pharmaceutically or physiologically acceptable acids, bases, alkali metals and alkaline earth metals.

In one embodiment, pharmaceutically acceptable salts can be formed from organic and inorganic acids including, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

In another embodiment, pharmaceutically acceptable salts may be formed from inorganic bases, desirably alkali metal salts including, e.g., sodium, lithium, or potassium, such as alkali metal hydroxides. Examples of inorganic bases include, without limitation, sodium hydroxide, potassium hydroxide, calcium hydroxide, and magnesium hydroxide. Pharmaceutically acceptable salts may also be formed from organic bases, such as ammonium salts, mono-, di-, and trimethylammonium, mono-, di- and triethylammonium, mono-, di- and tripropylammonium, ethyldimethylammonium, benzyldimethylammonium, cyclohexylammonium, benzyl-ammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmono-ethanolammonium, diethanolamine, ethylenediamine, and the like.

The salts, as well as other compounds, can be in the form of esters, carbamates and other conventional "prodrug" forms, which, when administered in such form, convert to the active moiety in vivo. In one embodiment, the prodrugs are esters. In another embodiment, the prodrugs are carbamates. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996), which is incorporated by reference.

An effective amount of the non-nutritive sweetener is administered to the patient. The term "effective amount" as used herein refers to a non-toxic amount of the non-nutritive sweetener. The effective amount will depend on the type of non-nutritive sweetener, patient's age, weight, height, or the like, unrelated or related medical conditions afflicted by the patient, condition being treated, among others. In some embodiments, the effective amount of non-nutritive sweetener is that which may be safely administered to the patient. In other embodiments, the effective amount of the non-nutritive sweetener is that set forth by the FDA.

Pharmaceutical compositions useful herein, in one embodiment, contain a non-nutritive sweetener in a pharmaceutically acceptable carrier or diluent with other optional suitable pharmaceutically inert or inactive ingredients.

The pharmaceutical compositions include a non-nutritive sweetener formulated neat or with one or more pharmaceutical carriers for administration, the proportion of which is determined by the solubility and chemical nature of the non-nutritive sweetener, chosen route of administration and standard pharmacological practice. The pharmaceutical carrier may be solid or liquid.

The non-nutritive sweetener may be administered by any permitted and approved means. In some embodiments, the non-nutritive sweetener is administered orally, nasally, transdermally, intravenously, subcutaneously, intramuscularly, intra-arterially, intraperitoneally, intracavitary, epidurally, or by infusion. In other embodiments, the non-nutritive sweetener is administered as a single dose. In further embodiments, the non-nutritive sweetener is administered as two or more doses. In still other embodiments, the non-nutritive sweetener is administered over a period of time such as by infusion. By administration via infusion, multiple CEST MRI or PET images may be obtained while simultaneously keeping a level of non-nutritive sweetener in the patient.

Although the non-nutritive sweetener may be administered alone, it may also be administered in the presence of one or more pharmaceutical carriers that are physiologically compatible. The carriers may be in dry or liquid form and must be pharmaceutically acceptable. In some embodiments, the liquid pharmaceutical compositions are sterile solutions or suspensions.

When liquid carriers are utilized, they may be sterile liquids. Liquid carriers are typically utilized in preparing solutions, suspensions, emulsions, syrups and elixirs. In some embodiments, the non-nutritive sweetener is dissolved a liquid carrier. In another embodiment, the non-nutritive sweetener is suspended in a liquid carrier. One of skill in the art of formulations would be able to select a suitable liquid carrier, depending on the route of administration. In one embodiment, the liquid carrier includes, without limitation, water, organic solvents, oils, fats, or mixtures thereof. In another embodiment, the liquid carrier is water containing cellulose derivatives such as sodium carboxymethyl cellulose. In a further embodiment, the liquid carrier is water and/or dimethylsulfoxide. Examples of organic solvents include, without limitation, alcohols such as monohydric alcohols and polyhydric alcohols, e.g., glycols and their derivatives, among others. Examples of oils include, without limitation, fractionated coconut oil, arachis oil, corn oil, peanut oil, and sesame oil and oily esters such as ethyl oleate and isopropyl myristate.

Alternatively, the non-nutritive sweetener may be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, the solid carrier may also act as a flavoring agent, lubricant, solubilizer, suspending agent, filler, glidant, compression aid, binder, disintegrant, or encapsulating material. Suitable solid carriers include, without limitation, calcium phosphate, dicalcium phosphate, magnesium stearate, talc, starch, sugars (including, e.g., lactose and sucrose), cellulose (including, e.g., microcrystalline cellulose, methyl cellulose, sodium carboxymethyl cellulose), polyvinylpyrrolidine, low melting waxes, ion exchange resins, and kaolin. The solid carrier can contain other suitable excipients, including those described below.

Examples of excipients which may be combined with the non-nutritive sweetener include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, the excipients described in the "Handbook of Pharmaceutical Excipients", 5$^{th}$ Edition, Eds.: Rowe, Sheskey, and Owen, APhA Publications (Washington, D.C.), Dec. 14, 2005, which is incorporated herein by reference.

D. Combination Therapies

The imaging methods, CEST MRI or PET, described herein may be performed in conjunction with conventional MRI methods. The term "conventional MRI" as used herein refers to any type of MRI that does not include CEST. The conventional MRI technique may be utilized in neuroimaging, cardiovascular MRI, musculoskeletal MRI, liver MRI, gastrointestinal MRI, functional MRI and oncological identification. In some embodiments, the conventional PRI includes, without limitation, anatomic proton-density weight, T1 weighted, T2 weighted, angiography, functional MRI, or combinations thereof.

Conventional MRI may be performed prior to, concurrently with, or subsequent to the CEST MRI or PET technique. When the CEST MRI methods and/or PET are supplemented by conventional MRI, the conventional MRI images are obtained similarly. Specifically, a baseline conventional MRI image of the patient is obtained. After administration of the non-nutritive sweetener, one or more conventional MRI images of the patient are then obtained. Comparison of the baseline conventional MRI image with the conventional MRI test image produces a final MRI image. In some embodiments, such comparisons with conventional MRI results provide complimentary information to the CEST MRI and/or PET result.

E. Application of the Methods

The baseline images, test images, and compared MRI, including CEST MRI and MRI images, i.e., final images, and/or PET images may be displayed over time in a medium sensible to an operator. One of skill in the art would be able to select media suitable for storing, comparing, and analyzing such images.

This final image may then be analyzed by the operator, radiologist, attending physician, or any other medical professional. The final image provides a display of areas in the patent where the non-nutritive sweetener has accumulated. In some embodiments, the non-nutritive sweetener accumulates in abnormal tissues. In other embodiments, the non-nutritive sweetener does not accumulate in normal tissues. In further embodiments, the non-nutritive sweetener accumulates in abnormal tissues at a higher rate than in normal tissue. In yet other embodiments, there is a measurable or quantifiable difference in the accumulation rates between normal and abnormal tissues. One of skill in the art would be able to determine if a difference in the accumulation rate is measurable or quantifiable. Accumulation of the non-nutritive sweetener in the abnormal regions may depend on a number of factors including, without limitation, diffusion, specific receptors, and transporters, angiogenesis, permeability, retention, among others. Accordingly, the final image highlights any of these abnormal regions. These regions may be discriminated based on the wash-in and wash-out rates of the sweeteners using the methods described herein. Accordingly, the methods described herein are useful for distinguishing abnormal tissue from normal tissue.

The term "abnormal" as used herein refers to tissue that is not indigenous to a subject. In some embodiments, the abnormal tissue includes, without limitation, neoplastic tissue, inflamed tissue, ischemic tissue, degenerated tissue, fibrotic tissue, among others, or combinations thereof. The neoplastic tissue may include any cancerous tissue type which may be visualized using CEST MRI or PET. The abnormal tissue may be localized or spread out in different areas of the patient. In some embodiments, the abnormal tissue is a tumor.

Accordingly, a number of various types of cancers may be detected using the methods described herein. In some embodiments, the cancer is adrenal cancer, anal cancer, bile duct cancer, bladder cancer, bone cancer, brain cancer, breast cancer, pediatric cancer, Castleman disease, cervical cancer, colorectal cancer, endometrial cancer, esophageal cancer, Ewing family, eye cancer, gallbladder cancer, gastrointestinal cancer, gestational trophoblastic disease, Hodgkin disease, Kaposi sarcoma, kidney cancer, laryngeal and hypopharyngeal cancer, leukemia, liver cancer, lung cancer, lymphoma, malignant mesothelioma, multiple myeloma, myelodysplastic syndrome, nasal cavity and paranasal sinus cancer, nasopharyngeal cancer, neuroblastoma, Non-Hodgkin lymphoma, oral cavity and oropharyngeal cancer, osteosarcoma, ovarian cancer, pancreatic cancer, penile cancer, pituitary cancer, prostate cancer, retinoblastoma, rhabdomyosarcoma, salivary gland cancer, sarcoma, skin cancer, small intestine cancer, stomach cancer, testicular cancer, thymus cancer, thyroid cancer, uterine cancer, vaginal cancer, vulvar cancer, waldenstrom macroglobulinemia, and Wilms tumor.

A variety of degenerative, fibrotic, ischemic, and inflamed tissue types may be visualized using the methods described herein. In some embodiments, the degenerative, fibrotic, ischemic, or inflamed tissue may be specific to one region of the patient. In other embodiments, the degenerative tissue, fibrotic, ischemic, or inflamed is may be a result to injury, aging, disease or normal wear and tear. In further embodiments, the tissue type is damaged cartilage, cardiovascular tissue including, e.g., myocardium tissue and heart tissue such as infarcted heart tissue, and fibrotic liver tissue, among others.

Not only may the non-nutritive sweeteners in combination with the CEST MRI or PET methods described herein useful in pinpointing areas of abnormal tissue in a patient, but the methods may also be used in treatment therapies. Specifically, non-nutritive sweeteners in combination with CEST MRI and/or PET methods may be utilized to determine if a particular treatment therapy is effective. In some embodiments, the methods described herein may be used to determine if a method of treating abnormal tissue is effective, i.e., useful in reducing or ameliorating a condition in a patient.

As such, the methods may be used in monitoring the effectiveness of a pharmaceutical agent, radiation, acupuncture, massage, physical therapy, among others, in treating the abnormal tissue. Accordingly, the methods described herein may, therefore, be effective in designing a therapy that effectively targets and treats the condition resulting in the abnormal tissue. When utilized for MRI, the methods may include the steps described herein including, without limitation, obtaining a baseline conventional MRI image and a baseline CEST MRI image of the patient, followed by administering a pharmaceutical agent to the patient. Thereafter, an effective amount of a non-nutritive sweetener is administered to the patient and a test CEST MRI image is obtained. When utilized for PET, the methods may include, without limitation, (i) administering a pharmaceutical agent to the patient, administering an effective amount of a non-nutritive sweetener comprising one or more radiolabels to the patient, and obtaining one or more positron emission tomography (PET) images of said patient.

One of skill in the art would be able to select a suitable timeframe, after administration of the pharmaceutical agent, for administering the non-nutritive sweetener and obtaining test CEST MRI and/or PET images.

"Treatment", or variations thereof, encompasses treatment of a subject clinically diagnosed as having a disease or medical condition. In one embodiment, the subject is treated and the disease or medical condition is eradicated, i.e., the subject is cured. As used herein, "prevention" encompasses prevention of symptoms in a subject who has been identified as at risk for the condition, but has not yet been diagnosed with the same and/or who has not yet presented any symptoms thereof.

The methods described herein are also indicated for analyzing the effect of a nutritive sugar on tumor cells in a patient. The term "nutritive sugar" as used herein refers to a chemical compound having one or two sugar molecules in the backbone and may be metabolized by a mammal. In some embodiments, the nutritive sugar is a monosaccharide or a disaccharide. In other embodiments, the nutritive sugar includes, without limitation, fructose, glucose, galactose, sucrose, lactose, and maltose. The MRI methods include obtaining a baseline CEST MRI image of the patient, administering a nutritive sugar to the patient, (iii) administering an effective amount of a non-nutritive sweetener to the patient, and obtaining a test CEST MRI image of the patient. The test image is then analyzed as described above and the effect of the nutritive sugar determined by one skilled in the art. The PET methods include administering a nutritive sugar to said patient, administering an effective amount of a non-nutritive sweetener comprising one or more radiolabel to said patient, and (iv) obtaining one or more positron emission tomography (PET) images of said patient. The test image is then analyzed as described above and the effect of the nutritive sugar determined by one skilled in the art.

The methods employing the non-nutritive sweeteners may also be used in analyzing a MRI contrast agent or PET radiotracer. The MRI contrast agent or PET radiotracer may be known in the art and FDA approved, such as gadolinium or radiolabeled contrast agents, or new MRI contrast agents or PET radiotracers. Accordingly, the non-nutritive sweetener methods may be useful in determining the effectiveness of MRI contrast agents or PET radiotracers, toxicity of MRI contrast agents or PET radiotracers, among others. In some embodiments, the methods of analyzing a MRI contrast agent include obtaining a baseline CEST MRI image of the patient, administering a MRI contrast agent to the patient, administering an effective amount of a non-nutritive sweetener to the patient; and obtaining a test CEST MRI image of the patient. The test image is then analyzed as described above and the effectiveness and/or safety of the MRI contrast agent determined by one skilled in the art. In other embodiments, the methods of analyzing a positron emission tomography (PET) radiotracer in a patient include administering a PET radiotracer to the patient, administering an effective amount of a non-nutritive sweetener comprising one or more radiolabel to the patient; and obtaining one or more PET images of the patient. The test image is then analyzed as described above and the effectiveness and/or safety of the PET radiotracer determined by one skilled in the art.

The methods described herein are also useful in analyzing the blood barrier of a patient. Thus, the methods and non-nutritive sweeteners discussed herein may be used in determining the integrity of the blood brain barrier (BBB). The term "blood brain barrier" as used herein refers to the semipermeable barrier which separates circulating blood from the fluid in the brain and which is composed of brain endothelial cells. In such methods, an effective amount of a non-nutritive sweetener comprising one more radiolabel is administered to the patient. By doing so, the amount of the non-nutritive sweetener which accumulates in the brain of the patent is measured. In some embodiments, the amount of non-nutritive sweetener accumulated in the brain is measured after the non-nutritive sweetener is administered. One of skill in the art would readily be able to determine the amount of non-nutritive sweetener which crosses the blood brain barrier.

One of more of the methods hereinbefore described may be effected on a patient. In some embodiments, methods of treating a patient using MRI and then PET, as described herein, are effected on the patient. In other embodiments, methods of using PET and then MRI, as described herein are effected on a patient. Such dual methods using both MRI and PET are useful in patients having a high blood glucose level. In some embodiments, the patient has a measured blood glucose level above normal as determined by those skilled in the art. In other embodiments, the patient has a measured blood glucose level of more than about 150 mg/DL.

F. Kits

Also provided herein are kits or packages of pharmaceutical formulations containing a non-nutritive sweetener or composition described herein. The kits may be organized to indicate a single formulation or combination of formulations to be taken at each desired time. The composition may also be sub-divided to contain appropriate quantities of the non-nutritive sweetener. For example, the unit dosage can be packaged compositions, e.g., packeted powders, vials, ampoules, prefilled syringes or sachets containing liquids.

Suitably, the kit contains packaging or a container with the non-nutritive sweetener formulated for the desired delivery route. Suitably, the kit contains instructions on dosing and an insert regarding the non-nutritive sweetener. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the delivery device. Other suitable components to include in such kits will be readily apparent to one of skill in the art, taking into consideration the desired indication and the delivery route. The doses are repeated daily, weekly, or monthly, for a predetermined length of time or as prescribed. The packaging means of a kit may itself be geared for administration, such as an inhalant, syringe, pipette, or other such like apparatus, by which the non-nutritive sweetener may be administered to the subject.

The non-nutritive sweetener or composition of these kits also may be provided in dried or lyophilized forms. When reagents or components are provided as a dried form, reconstitution generally is by the addition of a suitable solvent. It is envisioned that the solvent also may be provided in another packaging means.

The kits may include a means for containing the vials in close confinement for commercial sale such as, e.g., injection or blow-molded plastic containers into which the desired vials are retained.

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., and pressure is at or near atmospheric.

EXAMPLES

Example 1

Splenda Phantom Experiment

Different concentration of Splenda and sucralose were prepared in PBS and all the experiments were performed at 37° C. on a 9.4 T horizontal bore small animal MR scanner (Varian, Palo Alto, CA). CEST images were acquired at different saturation power and saturation lengths from frequency offset −5 to 5 ppm in step size of 0.1 ppm. Acquired CEST images were corrected for $B_0$ and used to generate CEST contrast map using Equation [1].

$$CEST(\%) = 100 \times \left[ \frac{S_{-ve} - S_{+ve}}{S_0} \right] \qquad \text{Eq [1]}$$

where $S_{-ve}$ and $S_{+ve}$ are the $B_0$ corrected MRI signals obtained at −1 ppm and +1 ppm respectively, and $S_0$ is the image obtained without any saturation. CEST contrast was further corrected for $B_1$ and mapped as false-colors onto anatomical proton image. The CEST asymmetry plots were generated by plotting the relative water signal difference at frequency offset from 0 to 4.8 ppm.

Figure 1:
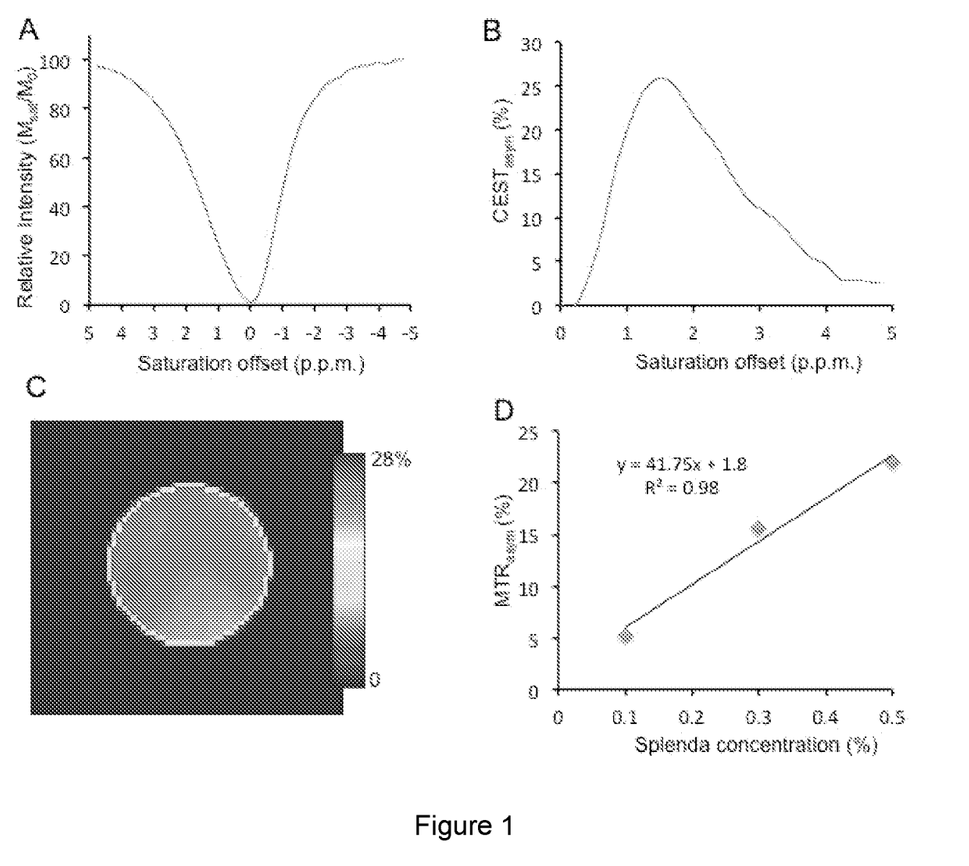
FIGS. 1A and 1B are, respectively, the Z-spectra and corresponding asymmetry plot from a solution containing 5% Splenda.
FIGS. 1C and 1D are the CEST map showing the CEST effect and line graph showing the concentration dependence of the CEST effect resulting from Splenda, respectively.

FIG. 1: Z-spectra (A), asymmetry plot (B), and CEST map (C) of CEST effect from 0.5% Splenda. The concentration dependence of CEST effect from Splenda is shown D.

Figure 2:
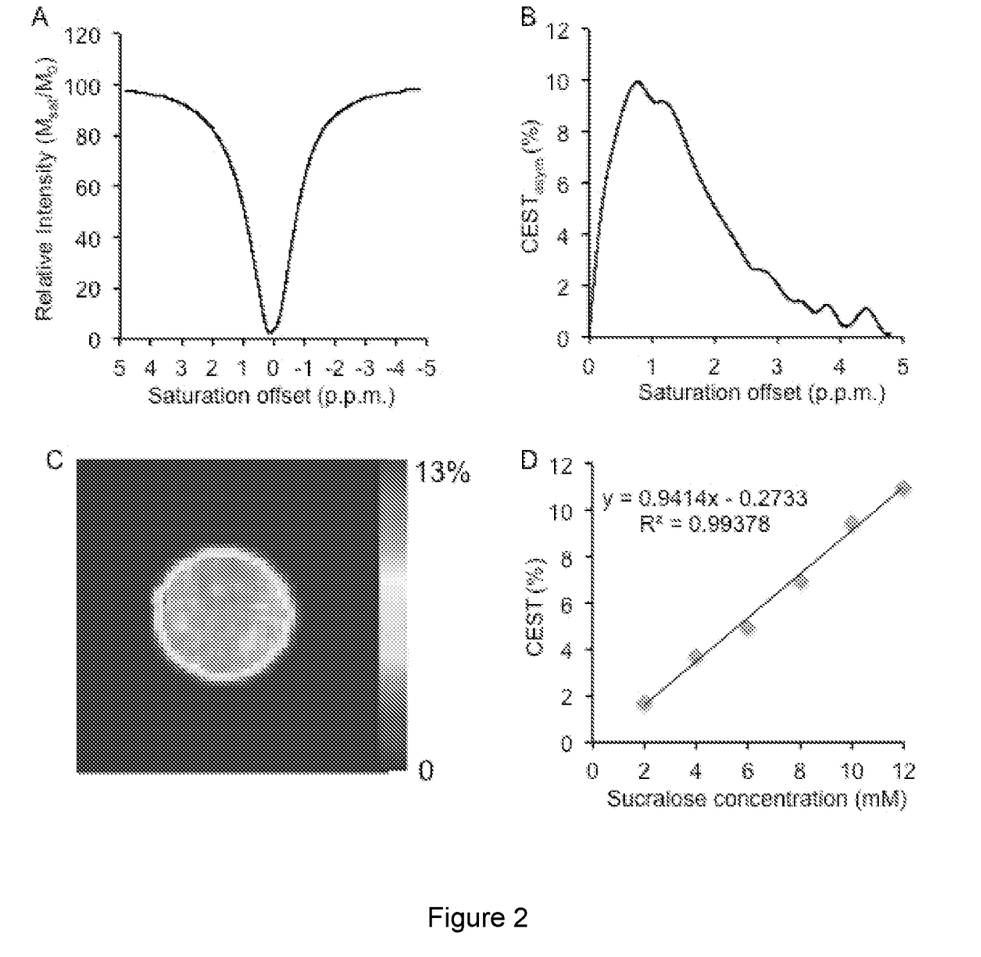
FIG. 2A is a Z-spectra from a 10 mM sucralose solution in PBS at 37° C. and pH 7
FIG. 2B is the corresponding asymmetry plot.
FIG. 2C is the CEST map of sucralose and FIG. 2D is the concentration dependence of the CEST from sucralose.

FIG. 2. A. Z-spectra from 10 mM sucralose solution in PBS at 37 C and pH 7. The corresponding asymmetry plot is shown in (B). C. Shows the CEST map of sweetener-sucralose. The concentration dependence of the CEST from sucralose is shown in D.

Example 2

Animal Tumor Model

Figure 3:
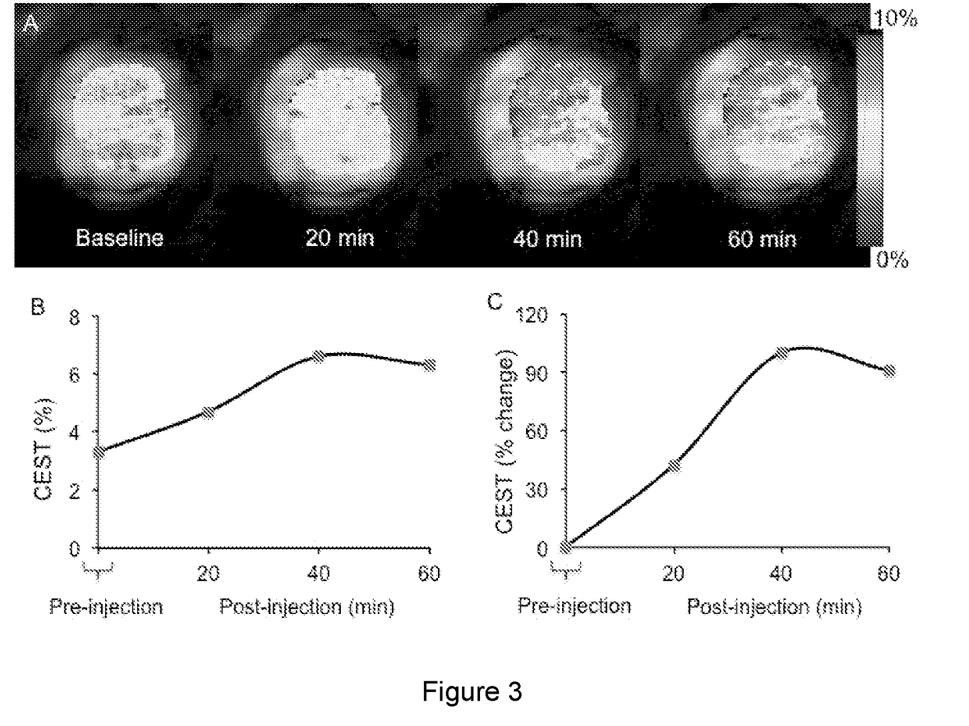
FIG. 3A is an image of a baseline and post sucralose injection into mouse tumors at 20, 40, and 60 minutes.
FIG. 3B is a line graph showing the pre-and post sucralose injected SWEETEST (SWEETEST is defined in Example 3, herein) contrast.
FIG. 3C is a line graph showing the percent change in the SWEETEST contrast post injection of sucralose.

Imaging was performed in tumor-bearing animals at a 9.4 T horizontal bore Varian system. The animal's body temperature was maintained at 37±1° C. with the air generated and blowing through a heater (SA Instruments, Inc., Stony Brook, NY). Respiration and body temperature were continuously monitored using a MRI-compatible small animal monitor system (SA Instruments, Inc., Stony Brook, NY). CEST imaging was performed using a custom-programmed, segmented radiofrequency GRE readout pulse sequence, with a frequency selective continuous wave saturation preparation pulse. CEST images were acquired before and after administration of sucralose. The CEST contrast maps were generated using the equation [1] as described above. Following CEST experiments, $T_1$-weighted images were acquired before and after administration of gadolinium-tetraazacyclododecanetetraacetic acid (Gd-DOTA) complex.

FIG. 3A shows the baseline and post sucralose injection (100 mM intra peritoneally) of tumor maps. A clear increase in contrast in tumor region can be seen in the sucralose images. FIG. 3B shows the pre-and post sucralose injected sucralose contrast. FIG. C provides the percent change in the contrast post injection of sucralose. At 40 minutes about 100% increase in sucralose contrast can be seen.

Example 3

Figure 4:
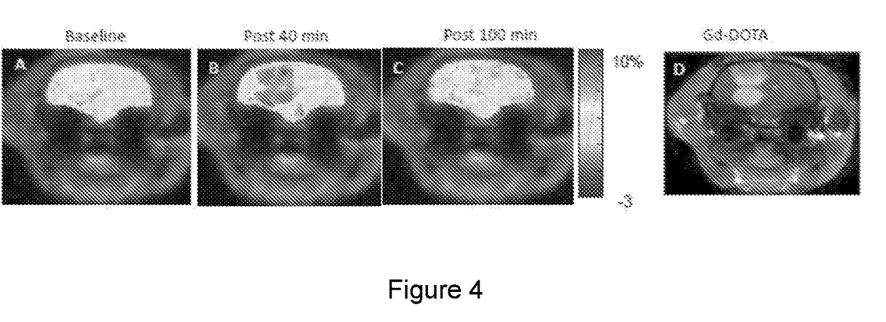
FIG. 4A is a baseline image prior to injection of sucralose.
FIGS. 4B and 4C are images at 40 and 100 minutes, respectively, post sucralose injection.
FIG. 4D is a Gd-DOTA enhanced MRI image of the same tumor.

FIG. 4. Sucralose injection studies in a rat brain tumor. Tumor region is indicated with a dash—A) CEST map at the baseline prior to injection of Sucralose. B) Sweetener Exchange Saturation Transfer (SWEETEST) map post injection of sucralose (300 mM) via tail vein. ~80% increase in SWEETEST contrast is seen at 40 minute post injection. After 100 minutes post injection, the SWEETEST map almost recovered to the baseline value (C). (D) Gd-DOTA enhanced MRI image of the same tumor. Althouth a SWEETEST map at 40 minutes post injection and Gd-DOTA enhanced MRI show comparable contrast in the tumor, the SWEETEST map also shows small contrast in peripheral regions of the tumor that are not visible in Gd-DOTA enhanced image.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed is:

1. An imaging method, comprising:
   (i) administering an effective amount of a non-nutritive sweetener, wherein the non-nutritive sweetener comprises aspartame, neotame, acesulfame, sucralose, cyclamate, saccharin, stevioside, rebaudioside, steviol, or combinations or derivatives thereof, to a patient; and
   (ii) subsequent to administering step (i), obtaining one or more images of a tissue of the patient where the non-nutritive sweetener has accumulated, the one or more images being derived from the presence of the non-nutritive sweetener in the tissue.

2. A magnetic resonance imaging (MRI) method, comprising:
   (i) obtaining a baseline chemical exchange saturation transfer (CEST) MRI image of a patient;
   (ii) administering an effective amount of a non-nutritive sweetener to said patient wherein the non-nutritive sweetener comprises aspartame, neotame, acesulfame, sucralose, cyclamate, saccharin, stevioside, rebaudioside, steviol, or combinations or derivatives thereof; and
   (iii) subsequent to the administration of step (ii), obtaining one or more test CEST MRI images of a tissue of the patient where the non-nutritive sweetener has accumulated wherein the step (i) and (iii) acquisition parameters are substantially the same and the one or more test CEST MRI images being derived from the presence of the non-nutritive sweetener in the tissue.

3. The magnetic resonance imaging method of claim 2, further comprising:
   (iv) comparing the baseline CEST MRI image to at least one test CEST MRI image to obtain a final image.

4. The magnetic resonance imaging method of claim 2, wherein step
   (i) further comprises obtaining a baseline conventional MRI image of said patient.

5. The magnetic resonance imaging method of claim 2, wherein step
   (iii) further comprises obtaining one or more test conventional MRI images of said patient.

6. The method of claim 2, wherein said non-nutritive sweetener accumulates in abnormal tissues.

7. The method of claim 6, wherein said abnormal tissue is neoplastic tissue, inflamed issue, ischemic tissue, degenerated tissue, or fibrotic tissue.

8. The method of claim 2, wherein said non-nutritive sweetener accumulates in abnormal tissues at a higher rate than in normal tissue.

9. The imaging method of claim 1 wherein the non-nutritive sweetener is sucralose.

10. The imaging method of claim 1, further comprising measuring an accumulation of the non-nutritive sweetener in an abnormal body tissue.

11. The imaging method of claim 1, further comprising measuring a rate of accumulation of the non-nutritive sweetener in an abnormal body tissue.

12. The imaging method of claim 1, wherein the one or more images are magnetic resonance images.

* * * * *